United States Patent [19]

Sommer et al.

[11] Patent Number: 4,868,128
[45] Date of Patent: Sep. 19, 1989

[54] PROCESS FOR DRY DISPERSAL OF PARTICLES, AND A DEVICE FOR CARRYING OUT THIS PROCESS

[75] Inventors: Karl Sommer, Palzing; Rolf Fath, Freising; Walter Peschke, Reiskirchen; Ulrich Bohnaus, Grossen-Linden, all of Fed. Rep. of Germany

[73] Assignee: Ernst Leitz Wetzlar GmbH, Wetzlar, Fed. Rep. of Germany

[21] Appl. No.: 112,507
[22] PCT Filed: Mar. 20, 1986
[86] PCT No.: PCT/DE86/00118
§ 371 Date: Aug. 20, 1987
§ 102(e) Date: Aug. 20, 1987
[87] PCT Pub. No.: WO87/03959
PCT Pub. Date: Jul. 2, 1987

[30] Foreign Application Priority Data

Dec. 23, 1985 [DE] Fed. Rep. of Germany ........ 3545865

[51] Int. Cl.⁴ .............................................. G01N 1/00
[52] U.S. Cl. ..................... 436/174; 422/99; 422/101; 422/63; 118/309
[58] Field of Search ................... 436/174; 422/99–102; 128/203.15; 401/137, 187–190; 427/180, 294; 118/50, 308, 309

[56] References Cited

U.S. PATENT DOCUMENTS

| | | | |
|---|---|---|---|
| 2,209,614 | 7/1940 | Rowley | 73/51 |
| 2,862,889 | 12/1958 | Mitchell | 252/359 |
| 3,362,405 | 1/1968 | Hazel | 128/203.15 |
| 3,472,202 | 10/1969 | Webb | 118/308 |
| 3,587,523 | 6/1971 | Tudor et al. | 118/309 |

FOREIGN PATENT DOCUMENTS

660107 5/1938 Fed. Rep. of Germany .
56-1336 3/1981 Japan .

OTHER PUBLICATIONS

The Leitz Autoscope P-the new problem solution for automatic particle analysis; Scientific and Technical Information, Achema 1985, Special Issue, pp. 22–25.

Primary Examiner—Barry S. Richman
Assistant Examiner—T. J. Wallen
Attorney, Agent, or Firm—Foley & Lardner, Schwartz, Jeffery, Schwaab, Mack, Blumenthal & Evans

[57] ABSTRACT

A process of dry dispersal of fine-grained particles on a specimen slide for the purpose of macroscopic or microscopic analysis, and a corresponding instrument for carrying out this process are described. The process permits random, homogeneous distribution of dry particles on a specimen slide in a unilayered, planar distribution, the particles not touching one another at all or only doing so to a negligible extent, i.e. being positioned on the speciment slide without agglomeration. The process steps are: metered input of the fine-grained substance into a sample container; aspiration of the substance by means of a defined partial vacuum, produced in a turbulence chamber, the substance reaching the turbulence chamber via an accelerator tube and then via a distributor tube, and deposition of the accelerated particles on a transparent speciment slide. The device can, in addition, contain a baffle, against which the powder-like sample substance is projected after rushing through the accelerator tube, in order to then pass through a distributor tube, from which the substance falls in deagglomerated form onto the specimen slide. The process and the device can be used for dry dispersal of a great variety of substances in mixed and pure form, for example foods, luxury foods and medicaments or the precursors thereof, mineral or industrial substances, medical or pharmaceutical preparations or precursors thereof, etc. The main area of application is the preparation of powder-like substances for automatic particle analysis.

20 Claims, 1 Drawing Sheet

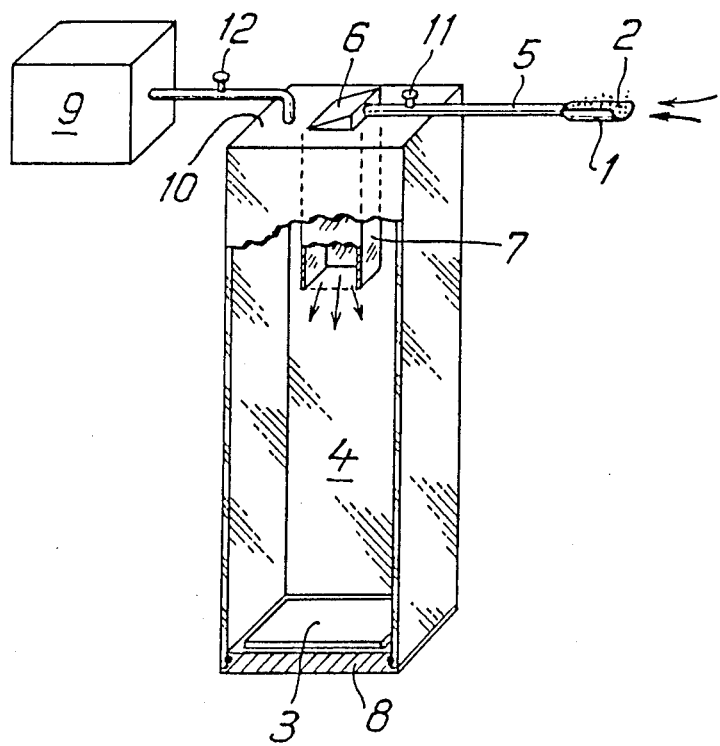

PROCESS FOR DRY DISPERSAL OF PARTICLES, AND A DEVICE FOR CARRYING OUT THIS PROCESS

BACKGROUND OF THE INVENTION

The invention relates to a process for dry dispersal of particles, and an instrument for dry dispersal of particles for producing on specimen slides a random, homogeneous fine distribution (a dispersal) of dry, fine, grainy bulk materials whose particle size distributions can be analyzed, for example, by means of automatic image analysis.

It is known that particles whose particle size distribution is to be determined by optical means through automatic image analysis must be dispersed perfectly in order to avoid so-called agglomerates (clotting-together of individual particles). Such agglomerations give rise to assessment errors and incorrect measurements. Likewise, two particles touching by chance on the specimen slide likewise simulate a (single) particle which is too large. In order to avoid these errors, it was hitherto necessary to apply the particles in highly dilute form - i.e. with a relatively large separation between the individual particles - to the specimen slide. However, the number of particles covered per image field is then impermissibly small or the evaluation times are too long. Fine powders cannot be formed on the specimen slide without agglomeration using conventional methods. The object of the present invention is therefore to provide a process and an instrument with which it becomes possible to disperse, in optimum fashion, fine, dry, grainy bulk goods (powders, dusts) and to apply them in the densest possible form onto a specimen slide, without the particles touching one another, so that such substances become more accessible for particle size determination by means of automatic image analysis.

BRIEF DESCRIPTION OF THE DRAWING

The drawing shows schematically an illustrative embodiment of the present invention.

DETAILED DESCRIPTION OF THE INVENTION

An enclosed space, designated as a turbulence chamber 4, in the form of a longitudinally prismatic hollow element contains, in the region of its top plate 10, a connector with a connecting line to a vacuum pump 9. When this vacuum pump is operated, a certain partial vacuum can be produced and maintained in the turbulence chamber 4. A distributor tube 7, which is connected, at its externally facing end region, directly to an accelerator tube 5, which has a shut-off valve 11, projects into the turbulence chamber 4. At the distal end of the accelerator tube 5 is located a trough-like or dish-like sample container 1 for the powder-like sample substance 2. The base plate 8 of the turbulence chamber 4 can be removed and has a circumambient vacuum-tight flange. On the base plate 8 is located at least one specimen slide 3. In the case represented, the cross-section of the turbulence chamber 4 and the cross-section of the distributor tube 7 is rectangular. However, other cross-section geometries are also possible. It is likewise possible for the distributor tube to have a cross-section which varies along its entire length. The axis of the distributor tube 7 can also be inclined to the axis of the vertical turbulence chamber 4; it is also possible for the part of the distributor tube 7 projecting into the turbulence chamber 4 to be variable in respect to its length.

According to a particularly expedient embodiment, a baffle 6, which can have a variable inclined position with respect to the vertical axis of the distributor tube 7 and the horizontal axis of the accelerator tube 5, is located in the end region of the distributor tube 7 leading to the outside.

The course of the process according to the invention is as follows: the sample container 1 is charged with a metered amount of a powder-like sample substance 2. The shut-off valve 11 is closed; with the pump valve 12 open, the vacuum pump 9 has produced a partial vacuum in the turbulence chamber 4, and this is maintained by closing the pump valve 12. If the shut-off valve 11 is now opened, a stream of air is drawn through the accelerator tube and then through the distributor tube. The stream of air carries the powder-like sample substance 2 along at a high speed, so that the particles, after leaving the distributor tube 7, rush through the remainder of the turbulence chamber at a relatively high speed and then hit the specimen slide 3. By means of the metering of the sample substance 2 into the sample container 1, it has already been ensured that a random, homogeneous planar distribution of the particles in the form of a planar unilayer is achieved on the specimen slide 3. If - as represented in the drawing - another inclined baffle 6, against which the powder-like sample substance 2 is projected, is located between the accelerator tube 5 and the actual distributor tube, an additional de-agglomeration effect is produced by this impact event. The particles to be prepared and subsequently to be analyzed are in a size range from 0.5 to 250 $\mu$m, preferably between 1 and 50 $\mu$m, and a settled bulk density range of 800 to 7,600 kg/m$^3$, preferably 400 to 2,000 kg/m$^3$. The level of the partial pressure to be produced in the turbulence chamber 4 is likewise dependent on the cross-section geometry of the individual components of the instrument according to the invention and on the particular sample substance 2 used. It must in any case be ensured that the particles in the accelerator tube 5 reach a speed of up to 100 m per second.

Planar particle distributions on the specimen slide 3 which have a degree of surface covering of up to 77% can be achieved by means of the process according to the invention. The great majority of all particles is deposited on specimen slide 3 in a fashion such that the individual particles do not touch one another. In this fashion, a specimen which can be used for automatic image analysis and whose individual components are present on the specimen slide in an insular position -i.e. de-agglomerated - is made available.

The following examples of powder-like sample substances can be dispersed in an optimum fashion by means of the process according to the invention or by means of the device according to the invention: baby powder, cocoa and milk powder, the starting components of chocolate bars, limestone, glass beads, mineral microfillers, kieselguhr, iron carbonyl inter alia.

We claim:

1. A process for dispersal of dry, fine-grained particles on a specimen slide in a unilayered, planar, random, homogeneous distribution comprising the following steps:
   (a) metering the particles into a sample container;
   (b) producing a partial vacuum in a turbulence chamber comprising a distributor tube connected to said sample container by an accelerator tube;

(c) aspirating the particles through the accelerator tube and the distributor tube; and (d) depositing the accelerated particles on a specimen slide located on the base plate of the turbulence chamber.

2. The process as claimed in claim 1, wherein the particles, after leaving the accelerator tube, are initially projected against a baffle before reaching the turbulence chamber via the distributor tube.

3. The process as claimed in claim 1, wherein the particles have a size range between 0.5 and 250 μm and a settled bulk density range between 400 and 7,600 kg/m$^3$.

4. The process as claimed in claim 1, wherein a particle speed of up to 100 meters per second is achieved in the accelerator tube.

5. The process as claimed in claim 1, wherein the degree of surface covering of the particles in an insular position on the specimen slide is up to 77%.

6. The process as claimed in claim 1, wherein the partial vacuum is optimized as a function of the respective particle size and type of particles.

7. A process as claimed in claim 1, wherein the particles have a size range between 0.5 and 250 μm and a settled bulk density range between 400 and 2,000 kg/m$^3$.

8. A device for depositing particles on a specimen slide in a unilayered, planar, random, homogeneous distribution, comprising:

(a) a turbulence chamber having a base plate and a top plate;

(b) a vacuum pump connected to the turbulence chamber for producing a vacuum in the chamber;

(c) at least one specimen slide arranged interchangeably on the base plate of the turbulence chamber;

(d) a distributor tube in the top plate of the turbulence chamber; and (e) an accelerator tube connected to the distributor tube.

9. The device as claimed in claim 8, wherein the distributor tube, at an end region projecting from the turbulence chamber, further comprises an inclined baffle with which the accelerator tube is aligned.

10. The device as claimed in claim 9, wherein the inclination of the baffle externally terminating the distributor tube can be varied with respect to the axis of the accelerator tube and the axis of the distributor tube.

11. The device as claimed in claim 8, wherein the accelerator tube additionally comprises a sample container on a distal end of the accelerator tube and a shut-off valve.

12. The device as claimed in claim 8, wherein the distributor tube has a rounded cross-section.

13. The device as claimed in claim 12, wherein the distributor tube has a longitudinal axis and wherein the cross-section of the distributor perpendicular to its longitudinal axis is selected from the group consisting of an ellipse and a circle.

14. The device as claimed in claim 8, wherein the distributor tube has an angular cross-section.

15. The device as claimed in claim 14, wherein the distributor tube has a longitudinal axis and wherein the cross-section of the distributor perpendicular to its longitudinal axis is selected from the group consisting of a square and a rectangle.

16. The device as claimed in claim 8, wherein the cross-sections of the distributor tube and of the turbulence chamber are geometrically similar.

17. The device as claimed in claim 8, wherein the part of the distributor tube located in the turbulence chamber has a cross-sectional area and a length such that an ideal planar distribution of the particles to be dispersed can be achieved on the specimen slide.

18. The device as claimed in claim 11, wherein the distributor tube comprises several casing segments which can be slid out of one another in the fashion of a telescope casing.

19. The device as claimed in claim 8, wherein the turbulence chamber has a longitudinal axis and the distributor tube projects into the turbulence chamber centrally and parallel to the longitudinal axis of the the turbulence chamber.

20. The device as claimed in claim 8, wherein the base plate is fixed interchangeably to an under side of the turbulence chamber and has a circumambient, vacuum-tight flange.

* * * * *